United States Patent [19]

Adini

[11] Patent Number: 4,823,610

[45] Date of Patent: Apr. 25, 1989

[54] DEVICE FOR AND METHOD OF MEASURING TENSILE FORCE IN REINFORCING MEMBER OF REINFORCED CONCRETE

[76] Inventor: Ari Adini, 104-20 Queens Blvd., Forest Hills, N.Y. 11375

[21] Appl. No.: 155,994

[22] Filed: Feb. 16, 1988

[51] Int. Cl.[4] .............................................. G01N 3/08
[52] U.S. Cl. ................................... 73/828; 73/862.42
[58] Field of Search ................ 73/826, 862.42, 862.48, 73/803, 828; 264/228; 403/43

[56] References Cited

U.S. PATENT DOCUMENTS 2,376,037  5/1945  Davies et al. ................. 73/862.42
3,868,850  3/1975  Davison et al. ............... 73/862.42

*Primary Examiner*—Jerry W. Myracle
*Attorney, Agent, or Firm*—Ilya Zborovsky

[57] ABSTRACT

A tensile stress in a reinforcing member of reinforced concrete is measured by reducing an initial tensile force in the reinforcing member substantially to zero, and measuring at this moment a tensile stress produced in an actuating unit with multiplying of the thus measured tensile stress by a cross sectional area of the actuating unit.

14 Claims, 1 Drawing Sheet

DEVICE FOR AND METHOD OF MEASURING TENSILE FORCE IN REINFORCING MEMBER OF REINFORCED CONCRETE

BACKGROUND OF THE INVENTION

The present invention relates to a device for and a method of measuring a tensile force in a reinforcing member in reinforced concrete, particularly prestressed reinforced concrete.

Prestressed reinforced concrete includes hardened cement paste, stone aggregates, and reinforcing members such as steel bars or strands which have been prestressed. The hardened mixture of the cement paste and aggregates offers excellent resistance to compressive stresses, but only low resistance to tensile stresses. Therefore the reinforcing members are embedded in the concrete in such areas that develop tensile stresses due to the superimposed loads on the structure. Methods of computations are known, which allow the design engineers to size structural members, such as beams, columns, slabs, etc. and allocate suitable amounts of steel reinforcement. There are situations when an engineer must determine the stress that prevails in the reinforcing steel elements in the existing structures. However, there are no methods and devices for performing such determinations.

SUMMARY OF THE INVENTION

Accordingly, it is an object of the present invention to provide a device and a method of measuring tensile force in a reinforcing member of reinforced concrete that allows determination of the tensile force in a simple and reliable manner without damaging the reinforcing element, so that it remains intact after the tests.

In keeping with these objects and with others which will become apparent hereinafter, one feature of the present invention is that an actuating unit is placed on a portion of a prestressed reinforcing member and then actuated so as to reduce an initial tensile force in the reinforcing member with an accompanied increased of a stress in the actuating unit, and when the tensile force in the reinforcing member is reduced substantially to a zero value, the stress in the actuating unit is measured and multiplied by its cross sectional area so as to obtain a value of the tensile force in the actuating unit which corresponds to the initial tensile force in the reinforcing member.

The novel features of the present invention are set forth in particular in the appended claims. The invention itself, both as to its construction and manner of operation will be best understood from the following description of preferred embodiments, which is accompanied by the following drawings.

DESCRIPTION OF PREFERRED EMBODIMENTS

Figure 1:
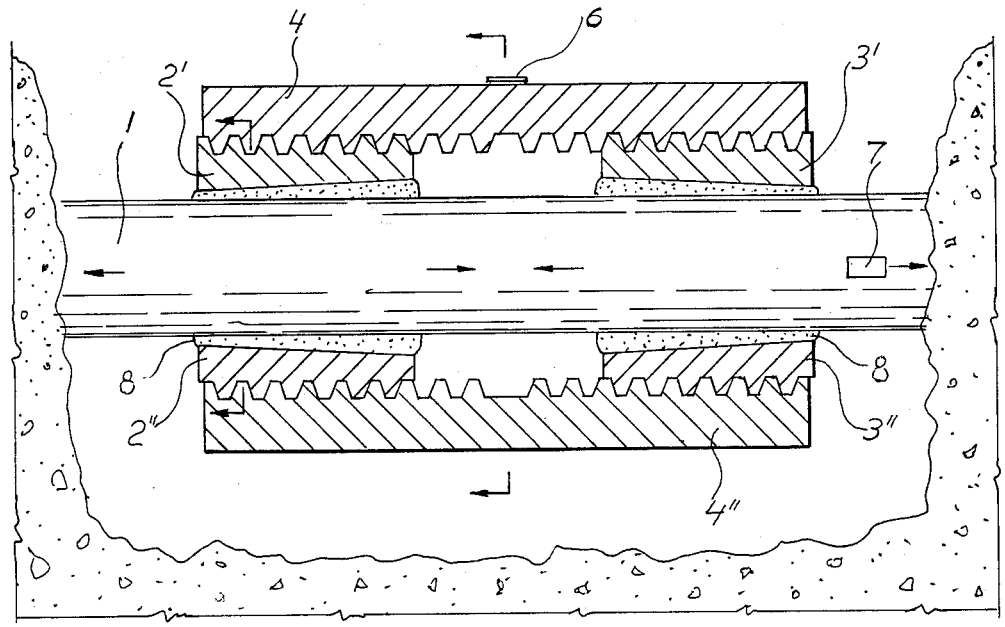
FIG. 1 is a view showing a portion of a reinforcing member in reinforced concrete with a device for measuring tensile forces in the reinforcing member, in accordance with the present invention.
Figure 2:
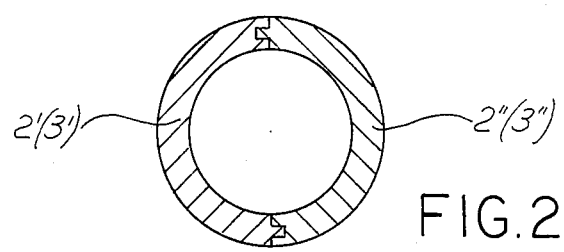
FIG. 2 is a view showing a cross section of one of two rings which are utilized in the inventive device.
Figure 3:
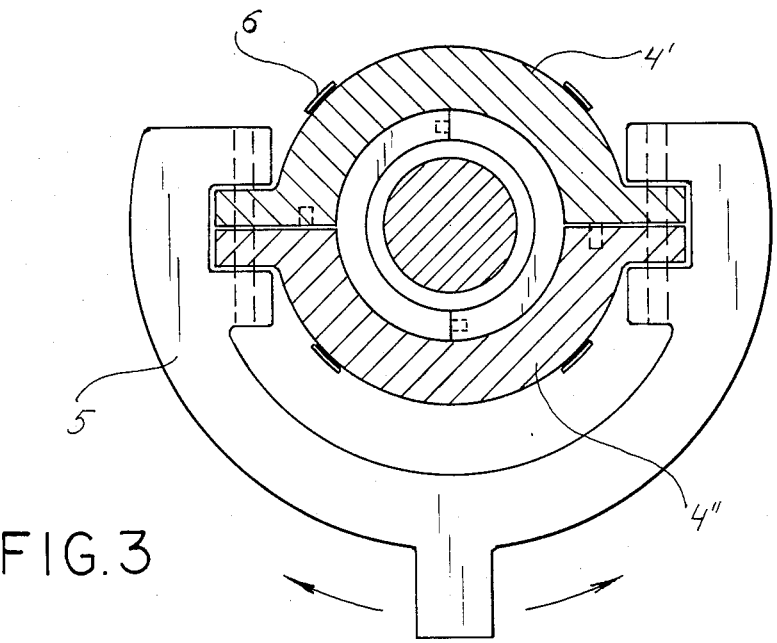
FIG. 3 is a view showing a cross section of a sleeve which surrounds the rings of the inventive device.

A device for measuring a tensile stress in a reinforcing member 1 of reinforced concrete has two rings 2 and 3 which are fitted on the reinforcing member. For this purpose, the rings are formed each of two semi-rings 2' and 2", and 3' and 3" respectively. The rings 2 and 3 have opposite threads on their outer surfaces.

A sleeve 4 surrounds the rings 2 and 3 and has in inner thread which engages with the outer thread of the rings. For placing the sleeve on the rings, the sleeve is also composed of two semi-sleeves 4' and 4". The semi-sleeves are provided with flanges which are connected with one another and with a handle 5 for example by screws. A plurality of strain gauges are arranged on the periphery of the sleeve 4 and uniformly distributed thereover. For the purpose of the measurement, a strain gauge is also arranged on the reinforcing member in its region outside the region between the rings. This additional strain gauge is identified as 7 The rings 2 and 3 and the sleeve 4 together form an actuating unit, the strain gauges 6 form means for measuring a stress in the actuating unit, and the gauge 7 forms means for indicating a moment when a tensile force in the reinforcing member 1 is reduced substantially to a zero value.

The measurements of the tensile force in the prestressed reinforcing member 1 is performed in the following manner:

The rings 2 and 3 are firmly attached to the portion of the reinforcing member 1, for example by epoxy adhesive 8. The sleeve 4 is placed onto the rings 2 and 3, and initially it is stress free. Then a user turns the sleeve 4 so that the rings 2 and 3 tend to move toward one another and compress the portion between them, thus reducing the tensile force in this portion of the reinforcing member. At the same time, the tensile stress increases in the sleeve 4 and is measured by the strain gauges 6. When the tensile force in this portion of the reinforcing member reaches zero and just starts to be reversed, the strain gauge 7 will show an increase in stress in the outside portion. At this particular point, the tensile stress in the sleeve will be exactly equal to the value of the initial tensile stress in the reinforcing member. The tensile stress measured by the strain gauges 6 and averaged for higher accuracy is then multiplied by the cross sectional area of the sleeve and gives the total tensile forced of the sleeve and, in other words, the initial tensile force in the reinforcing member.

The present invention is not limited to the details shown since various modifications and structural changes are possible without departing from the spirit of the invention.

What is desired to be protected by Letters Patent is set forth in particular in the appended claims.

I claim:

1. A device for measuring a tensile force of a reinforcing member arranged in reinforced concrete, comprising
   an actuating unit arranged to be placed on a portion of a reinforcing member in a reinforced concrete and to reduced an initial tensile force of the reinforcing member with an accompanying increase of a stress in said actuating unit;
   means arranged to be placed on another portion of the reinforcing member for indicating a moment when the tensile force is reduced to a zero value; and
   means arranged on said actuating unit for measuring the stress of said actuating unit when said indicating means indicates the moment of reduction of the tensile force in the reinforcing member substantially to zero, the thus measured stress in said actuating unit at said moment, being multiplied by a cross sectional area of said actuating unit, is a measure of the initial tensile force of the reinforcing member.

2. A device as defined in claim 1, wherein said actuating unit includes two rings arranged to be placed on the portion of the reinforcing member at a distance from one another and having opposite threads, and a sleeve surrounding said rings and having an inner thread engaging with said threads of said rings, so that upon turning of said sleeve said rings move toward one another and compress the reinforcing member so as to reduce the initial tensile force in the latter.

3. A device as defined in claim 2, and further comprising means for fixedly attaching said rings to the portion of the reinforcing member.

4. A device as defined in claim 3, wherein said means for fixedly attaching said rings to the portion of the reinforcing member includes a layer of adhesive.

5. A device as defined in claim 2, wherein each of said rings has at least one separating point so as to faciltate placing said rings on said portion of said reinforcing member.

6. A device as defined in claim 2, wherein said sleeve has at least one separating point so as to facilitate placing said ring on said rings of said actuating unit.

7. A device as defined in claim 2, wherein each of said ring is composed of two semi-rings connectable with one another, for facilitating placing said sleeve on said rings of said actuating unit.

8. A device as defined in claim 7, wherein said semi-rings have flanges alignable with one another; and further comprising connecting means for connecting said semi-rings with one another and including connecting elements extending through said flanges.

9. A device as defined in claim 2, and further comprising a handle connected with said sleeve and adapted to be grasped by a user so as to turn said sleeve.

10. A device as defined in claim 1, wherein said means for measuring the stress in said actuating unit is arranged on and operative for measuring the stress in said sleeve during the turning of said sleeve for moving said rings toward one another.

11. A device a defined in claim 10, wherein said means for measuring the stress includes a plurality of strain gauges arranged on and distributed over a periphery of said sleeve.

12. A device as defined in claim 1, wherein said means for indicating a moment when the tensile force is educed substantially to a zero value includes an indicating element located on another portion of the reinforcing member, which is laterally outside of said first-mentioned portion, so as to indicate a moment of increase of a tensile force in the other portion which corresponds to the moment of the reduction of the tensile force in said first-mentioned portion to zero.

13. A device as defined in claim 12, wherein said indicating element is formed as a strain gauge attachable to said other portion of the reinforcing member laterally outside of said first-mentioned portion.

14. A method of measuring a tensile force of a reinforcing member in reinforced concrete, comprising the steps of placing an actuating unit on a portion of a reinforcing member in reinforcing concrete;

actuating the actuating unit so as to reduce an initial tensile force in the reinforcing member with an accompanied increase of a stress in the actuating unit;

indicating a moment when the tensile force in the reinforcing member is reduced substantially to a zero value; and measuring the stress in the actuating unit when said moment is indicated, so that the thus measured stress in the actuating unit multiplied by a cross sectional area of the actuating unit gives a measure of the initial tensile stress of the reinforcing member.

* * * * *